(12) United States Patent
Brooks

(10) Patent No.: US 6,884,254 B2
(45) Date of Patent: Apr. 26, 2005

(54) TOURNIQUET SYSTEM

(76) Inventor: Shan L. Brooks, 1826 Fox Ct., Wellington, FL (US) 33414

( * ) Notice: Subject to any disclaimer, the term of this patent is extended or adjusted under 35 U.S.C. 154(b) by 275 days.

(21) Appl. No.: 10/056,838

(22) Filed: Jan. 25, 2002

(65) Prior Publication Data

US 2003/0028215 A1 Feb. 6, 2003

Related U.S. Application Data

(60) Provisional application No. 60/309,831, filed on Aug. 3, 2001.

(51) Int. Cl.[7] .............................................. A61B 17/132
(52) U.S. Cl. ........................ 606/201; 606/203; 24/71 R
(58) Field of Search ................................ 606/203, 201, 606/202; 24/71 R, 71 ST, 71 SB, 69 ST, 69 SB, 191, 309, 170

(56) References Cited

U.S. PATENT DOCUMENTS

| | | | | |
|---|---|---|---|---|
| 1,522 A | * | 3/1840 | Fogg | .......................... 26/105 |
| 947,284 A | * | 1/1910 | Sourek | ......................... 24/170 |
| 1,057,714 A | * | 4/1913 | Davis | ........................ 24/71 ST |
| 1,092,203 A | * | 4/1914 | Carter | ....................... 24/69 ST |
| 2,893,394 A | * | 7/1959 | Thomsen | ..................... 606/203 |
| 3,605,204 A | * | 9/1971 | Amundsen | .................... 24/171 |
| 4,125,115 A | | 11/1978 | Mayo et al. | |
| 4,670,946 A | * | 6/1987 | Olivieri | .................... 24/71 SK |
| 4,843,688 A | * | 7/1989 | Ikeda | ........................... 24/170 |
| 5,001,847 A | * | 3/1991 | Waters | ....................... 36/50.1 |
| 5,181,280 A | * | 1/1993 | Zachry, Jr. | ...................... 2/452 |
| 5,451,234 A | * | 9/1995 | Wassermann | ................ 606/203 |
| 5,592,722 A | * | 1/1997 | Foscaro et al. | ........... 24/68 SK |
| 6,053,169 A | | 4/2000 | Hunt | |
| 6,311,372 B1 | * | 11/2001 | Wang | ...................... 24/71 SK |
| 6,499,197 B1 | * | 12/2002 | Huang | ..................... 24/68 CD |

* cited by examiner

Primary Examiner—Anhtuan T. Nguyen
Assistant Examiner—Bradford C Pantuck
(74) Attorney, Agent, or Firm—Akerman Senterfitt

(57) ABSTRACT

A tourniquet system having a strap, a clamp for selectively engaging the strap in which once the clamp engages the strap, the clamp permits the strap to pass substantially freely in a direction away from the clamp and substantially prevents the strap from passing in a direction towards the clamp and securing structure attached to the strap for securing the strap.

10 Claims, 5 Drawing Sheets

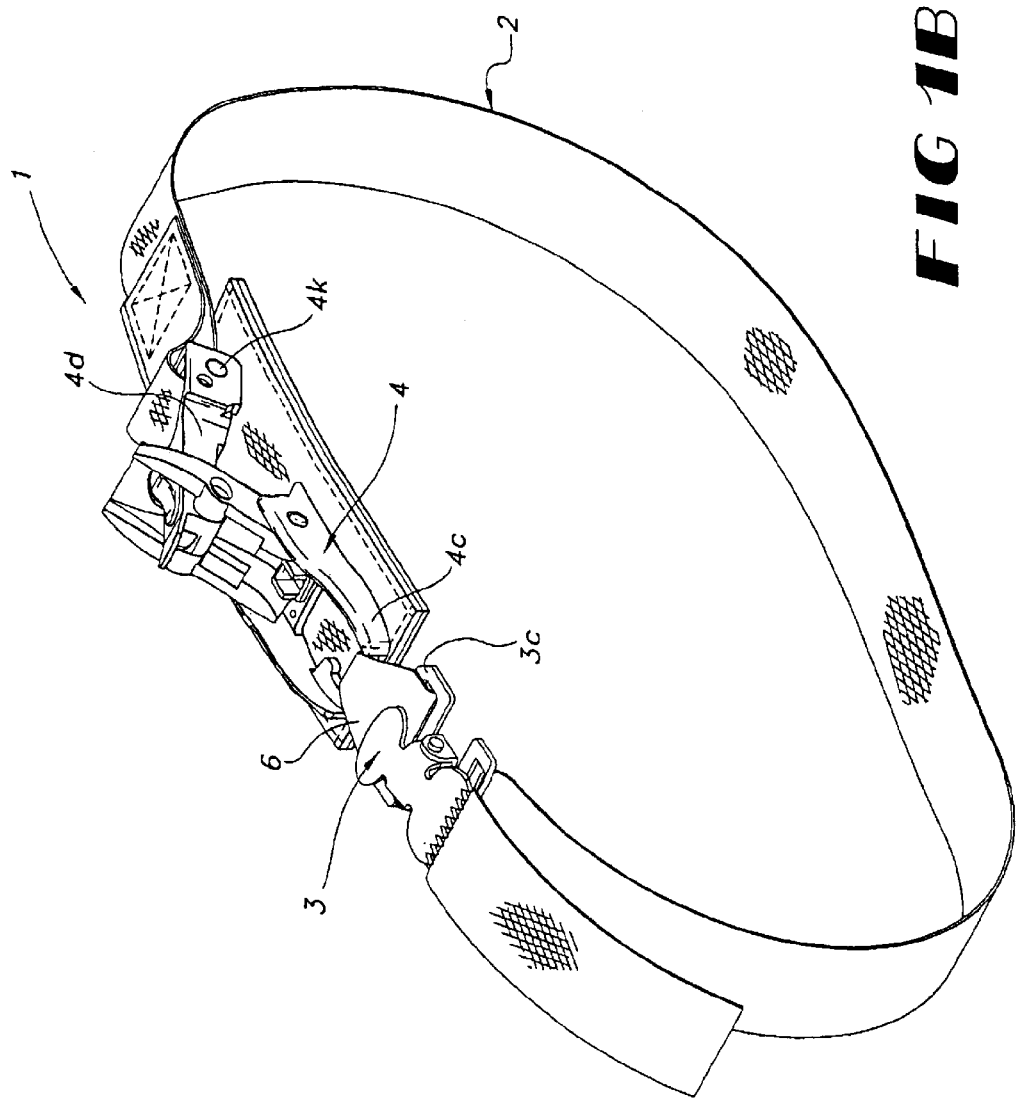

TOURNIQUET SYSTEM

CROSS-REFERENCE TO RELATED APPLICATIONS

This application claims priority of U.S. Provisional Application No. 60/309,831 filed on Aug. 3, 2001.

STATEMENT REGARDING FEDERALLY SPONSORED RESEARCH OR DEVELOPMENT (Not Applicable)

BACKGROUND

1. Technical Field

The present invention relates generally to medical equipment, and more particularly to emergency life-saving medical equipment used to treat severe wounds.

2. Description of Related Art

Tourniquets have been used for a number of years to stop excessive bleeding from severe wounds. Many tourniquets are simply pieces of rope or cord that can be tied around an extremity that has been severely damaged. In addition, other tourniquets have been developed such as those constructed of nylon with "VELCRO" patches to eliminate the need for tying a knot in the tourniquet. Although useful for stopping such heavy bleeding, applying either of these tourniquets may be awkward or difficult for the injured person. As a result, for purposes of properly securing the tourniquet, a second person may be needed to assist the victim. This may be impossible as the wounded person may be alone and may not have enough time to seek help from another individual. Thus, what is needed in the art is a tourniquet system that overcomes the limitations of the prior art without significantly increasing costs or design complexity.

SUMMARY OF THE INVENTION

The present invention concerns a tourniquet system capable of being operated by a single user. According to one aspect of the invention, the tourniquet system includes a strap, a clamp for selectively engaging the strap in which when the clamp engages the strap, the clamp permits the strap to pass substantially freely in a direction away from the clamp and substantially prevents the strap from passing in a direction towards the clamp and securing structure attached to the strap for securing the strap. In one arrangement, the securing structure can further secure the strap when the clamp engages the strap.

In one aspect of the invention, the securing structure can include a cover having at least one pin and at least one aperture, a base having at least one aperture and a traveling arm having at least one pin in which the cover pin can be rotatably coupled to the base apertures and the traveling arm pin can be rotatably coupled to the cover apertures. In addition, the securing structure can include a lock for securing the cover and the traveling arm to the base. The cover can also include: a slot for receiving the traveling arm; an opening for receiving a projection for lifting the cover.

In another arrangement, the base can include a first securing bar and the traveling arm can include a second securing bar in which the strap can be attached to the first securing bar. Additionally, the tourniquet system can include a supplemental strap attached to the clamp and the second securing bar of said traveling arm. The strap can be constructed of flexible webbing.

The invention also concerns a method of applying a tourniquet. In one aspect of the invention, the method includes the steps of inserting a limb into a strap, selectively engaging the strap such that the strap is permitted to pass substantially freely in a first direction and substantially prevented from passing in a second direction in which the second direction is substantially opposite of the first direction and securing the strap in which the inserting, engaging and securing steps are capable of being performed by a single user. In one aspect, the method can include the step of further securing the strap after the selectively engaging step is performed.

In one arrangement, the method can also include the steps of providing a securing structure for securing the strap in which the securing structure has a cover having at least one pin and at least one aperture, a base having at least one aperture and a traveling arm having at least one pin, rotatably coupling the cover pin to the base apertures and rotatably coupling the traveling arm pin to the cover apertures. In another arrangement, the base can have at least one snap projection, and the securing the strap step can include the steps of pulling the cover towards the base thereby causing the traveling arm to be forced towards the base and engaging the snap projections of the base to the cover apertures thereby securing the cover and the traveling arm to the base.

The method can also include the step of providing a lock for locking the cover and the traveling arm to the base in which the securing the strap step further includes the step of locking the lock to lock the securing structure in place. In another aspect, the cover can include an opening for receiving a projection, and the method can further include the steps of unlocking the lock, inserting the projection into the opening and lifting the projection to move the cover and traveling arm away from the base thereby disengaging the securing structure.

BRIEF DESCRIPTION OF THE DRAWINGS

FIG. 1B is a perspective view of an alternative tourniquet system in accordance with the inventive arrangements.

DETAILED DESCRIPTION OF THE PREFERRED EMBODIMENTS

Figure 1A:
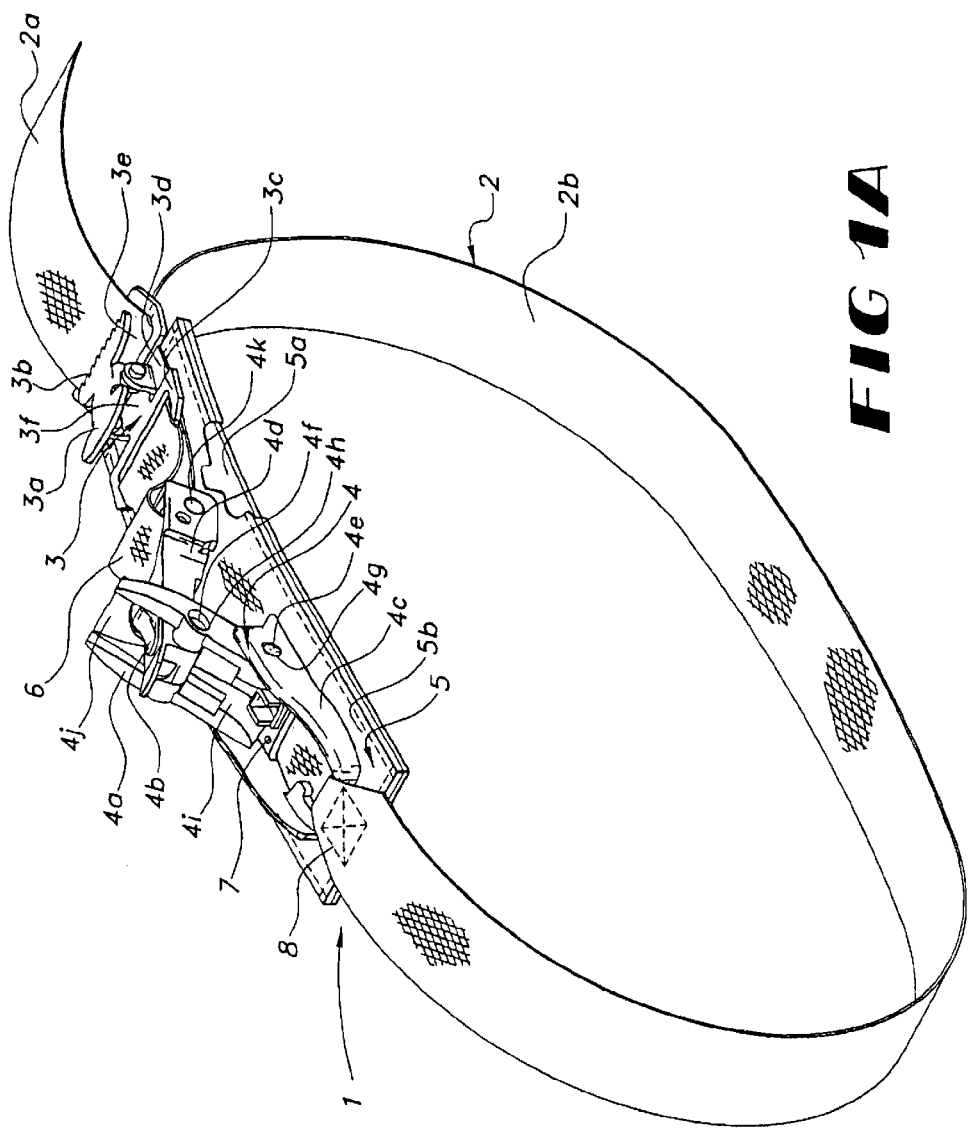
FIG. 1A is a perspective view of a tourniquet system in accordance with the inventive arrangements.

FIG. 1 A illustrates a tourniquet system 1, which can be used to stop excessive bleeding from a limb. The system 1 can include a main strap 2, a clamp 3, a securing structure 4 and a first elongated base 5. As shown in FIG. 1A, the first elongated base 5 can include a piece of rigid, flexible material 5a such as plastic or malleable metal surrounded by a flexible wrapping 5b. As an example, the flexible wrapping 5b can be polypropylene webbing. Constructing the first elongated base 5 in this manner can make the base relatively comfortable and flexible without severely diminishing the rigidity of the first elongated base 5. It should be noted, however, that the system 1 is not limited in this regard, as the first elongated base 5 can be constructed of any other suitable materials. In addition, it is not necessary to completely surround the rigid, flexible material 5a with the wrapping 5b. The first elongated base 5 is also not limited to the configuration illustrated in FIG. 1A, as the first elongated base 5 can have a width that is equal to or narrower than the width of the strap 2.

The securing structure 4 can be attached to the first elongated base 5 and can be used to engage or disengage the system 1. The securing structure 4 can be attached to the first elongated base 5 by one or more fasteners 7 such as one or more rivets; however, the system 1 is not limited in this regard, as any other suitable means can be used to attach the securing structure 4 to the first elongated base 5. Additionally, the securing structure 4 can contain a cover 4a, a base 4c and a traveling arm 4d. The securing structure 4 can also have a lock 4b, which can be used to secure the cover 4a and the traveling arm 4d to the base 4c.

In one arrangement, the cover 4a can have one or more pins 4e, which can be rotatably coupled to one or more corresponding apertures 4g contained within the base 4c. Further, the traveling arm 4d can have one or more pins 4f, which can be rotatably coupled to one or more corresponding apertures 4h contained within the cover 4a. In another arrangement, the pins 4f preferably do not extend beyond the outer surface of the apertures 4h thereby leaving a shallow area between the end of each of the pins 4f and the outer surface of each of the apertures 4h. The base 4c can also include one or more projections (not shown), which can snap engage the apertures 4h of the cover 4a as a result of the space between the outer surface of the apertures 4h and the ends of the pins 4f. In addition, the cover 4a can have a slot 4i for receiving the traveling arm 4d and an opening 4j for receiving a projection such as a finger or a tool, which can be used to lift the cover 4a. It is understood, however, that the invention is not limited to this particular securing structure as illustrated in FIG. 1A, as any other suitable securing structure can be incorporated into the invention.

The main strap 2 can be attached to the first elongated base 5. In one arrangement, the base 4c can contain a first securing bar (not shown) around which the main strap 2 may be looped. Once the strap 2 is looped, the end of the main strap 2 can be attached to itself and the first elongated base 5. As an example, once looped, the main strap 2 can be secured to the first elongated base 5 through the employment of a box stitch 8; however, the main strap 2 can be attached to the first elongated base 5 by any other suitable means of attachment. In one embodiment, the main strap 2 can be constructed of a flexible webbing such as nylon. The main strap 2, however, can also be any other suitable flexible yet durable material.

The traveling arm 4d can include a second securing bar 4g around which a supplemental strap 6 can be looped. The supplemental strap 6 can also be looped around a receiving structure 3c attached to the clamp 3. The supplemental strap 6 can then be secured to a second elongated base 3d. As an example, the ends of the supplemental strap 6 can be secured or stitched to one another and to a separate portion of the supplemental strap 6, and the ends of the supplemental strap 6 and the separate portion can then be secured or stitched to the second elongated base 3d. The invention is not limited in this regard, however, as the supplemental strap 6 can be secured to the second elongated base 3d by any other suitable structure.

The clamp 3 can be used to engage a suitable portion of the main strap 2. In one arrangement, the clamp 3 can contain the receiving structure 3c, which, as discussed above, can be used to secure the clamp 3 to the supplemental strap 6, and an engaging structure 3a. The engaging structure 3a can be used to engage selectively a portion of the strap 2. As pictured, once the engaging structure 3a engages the strap 2, a loop 2b can be formed through which an injured limb to which the system 1 will be secured may pass. The engaging structure 3a can include a clamp base 3f, a slotted opening 3e attached to the clamp base 3f and a grasping structure 3b. In addition, the grasping structure 3b of the engaging structure 3a can grasp a portion of the strap 2 that has passed through the slotted opening 3e.

In one arrangement, once the grasping structure 3b has grasped a particular section of the strap 2, the grasping structure 3b of the engaging structure 3a can permit the strap 2 to pass freely in a first direction yet can inhibit the strap 2 from passing in a second direction opposite to that of the first direction. That is, once the user has passed his limb through the loop 2b and the grasping structure 3b has grasped a section of the strap 2, the user can pull a free end 2a of the strap 2 thereby causing the strap 2 to pass through the slotted opening 3e and tightening the loop 2b without the user having to operate the clamp 3. Further, once the user is satisfied with the fit of the loop 2b, the grasping structure can prevent the strap 2 from passing back through the slotted opening 3e thereby preventing the accidental loosening of the loop 2b.

In another arrangement, the user can loosen the loop 2b simply by disengaging the grasping structure 3b from the strap 2 and pulling a portion of the strap 2 through the slotted opening 3e to increase the circumference of the loop 2b. Although FIG. 1A illustrates the engaging structure 3a as an alligator teeth type clasp in which the grasping structure 3b is a set of alligator teeth designed to permit the strap to pass freely in one direction but not in an opposite direction once the teeth grasp the strap 2, the invention is not so limited. In fact, the grasping structure 3b can be any structure suitable for adjustably grasping the strap 2 in accordance with the above discussion. In another arrangement, the clamp 3 can be constructed of a durable metal for improving the strength of the clamp 3. The clamp 3, however, can be constructed of other suitable materials.

FIG. 1B illustrates an alternative arrangement of the system 1. As can be seen in FIG. 1B, the clamp 3 can be positioned on the opposite end of the securing system 4 such that the clamp 3 is connected to the base 4c of the securing system 4. Specifically, the supplemental strap 6 that can be looped around the receiving structure 3c attached to the clamp 3 can also be looped around the first securing bar (not shown) of the base 4c. The opposite end of the strap 2 can be attached to the second securing bar 4g of the traveling arm 4d. In one arrangement, the end of the strap 2 can be looped around the second securing bar 4g and can be stitched to an appropriate section of the strap 2. Although structurally dissimilar, the overall operation of the clamp 3 and the securing structure 4 in this arrangement, for purposes of tightening or loosening the strap 2 to an injured limb, can be similar to the operation of the clamp 3 and securing structure 4 as described in connection with FIG. 1A and the subsequent figures discussed below.

Figure 2:
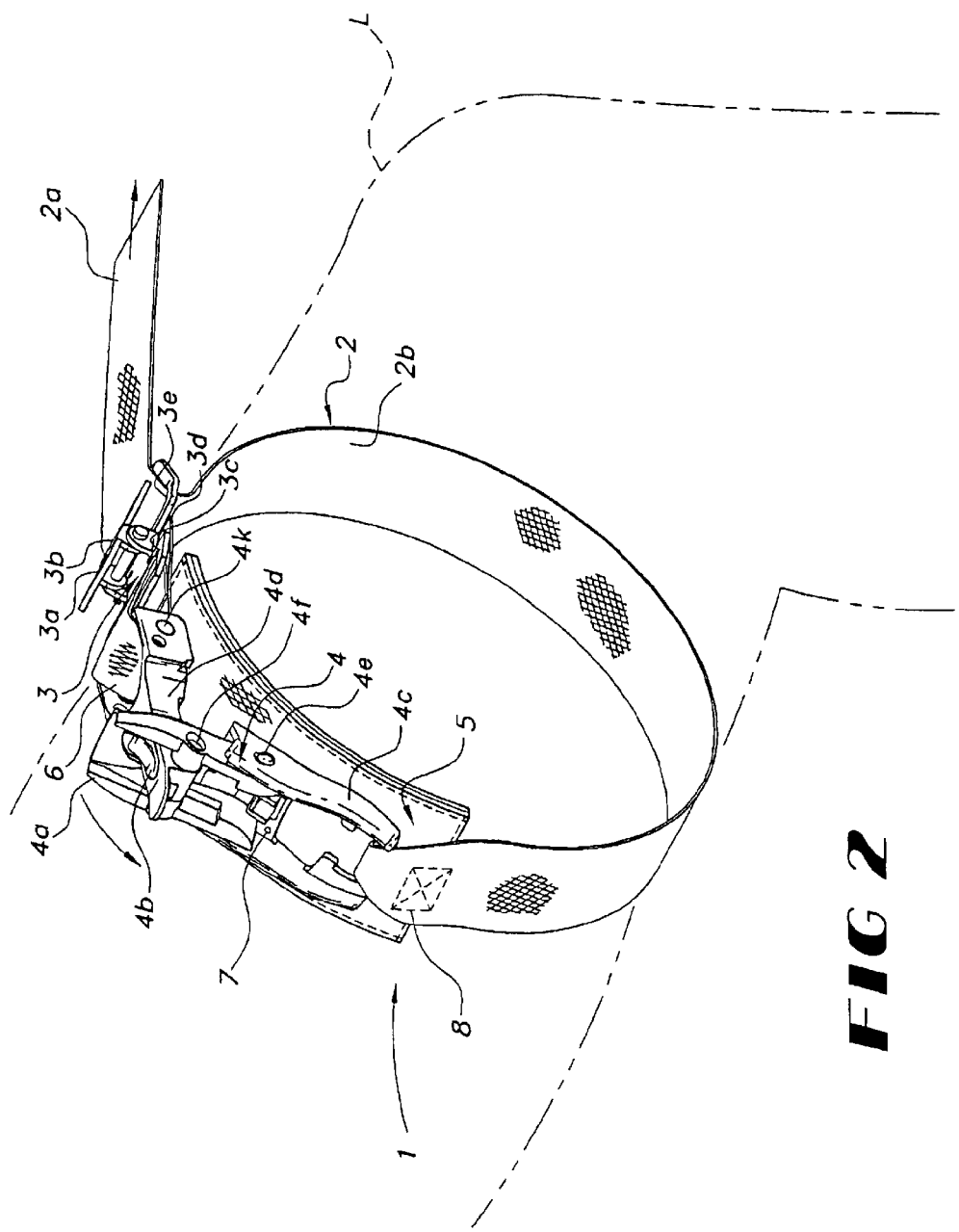
FIG. 2 illustrates the tourniquet system of FIG. 1A positioned around a person's limb prior to being secured to the limb.

Referring to FIG. 2, the system 1 is shown as the system 1 is being attached to a limb L. Specifically, the securing structure 4 can be in a disengaged position such that the cover 4a and the traveling arm 4d are extended away from the base 4c. If necessary, the grasping structure 3b can be disengaged to increase the circumference of the loop 2b to permit a user to pass their injured limb freely through the loop 2b. Once the injured limb L is passed through the loop 2b, the user can pull the free end 2a of the strap 2 away from the clamp 3. This process can tighten the strap 2 around the injured limb L, and once the strap 2 is suitably secured to the injured limb L, the user can cease pulling the free end 2a of the strap 2, and the grasping structure 3b can then automatically secure the strap 2 in place.

Figure 3:
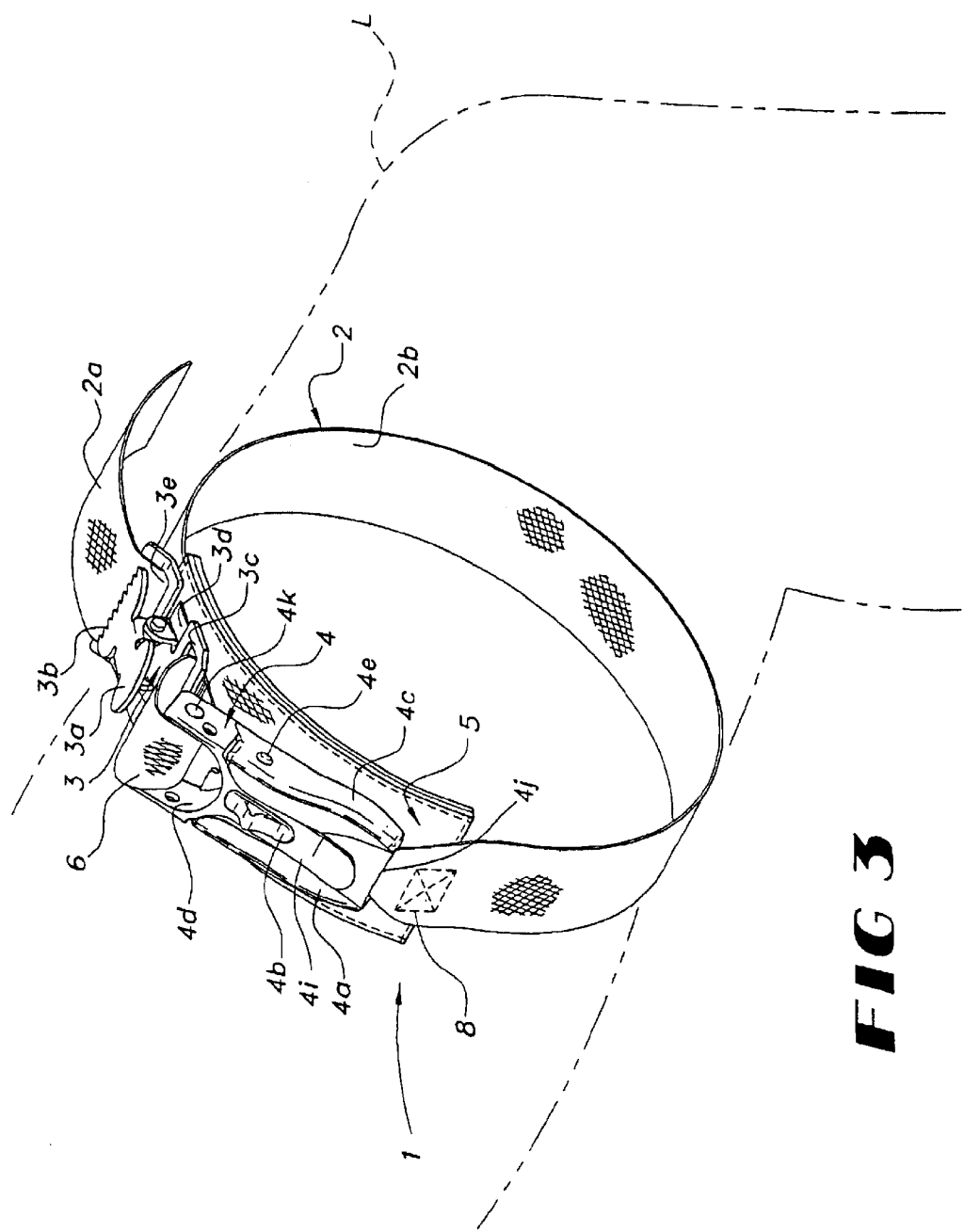
FIG. 3 illustrates the tourniquet system of FIG. 1A positioned around and secured to a person's limb.

As shown in FIG. 3, once the strap 2 has been suitably positioned and tightened, the user can then engage the securing structure 4, which can further secure the system to the injured limb L. The securing structure 4 is engaged by pulling the cover 4a towards the base 4c. As the cover 4a is pulled towards the base 4c, the traveling arm 4d is also directed towards the cover 4a and fits within the slotted opening 4i. Subsequently, the cover 4a and the traveling arm 4d can be secured to the base 4c by snap engaging the projections (not shown) of the base 4c with the apertures 4h (not shown) of the cover 4a. The user can then engage the lock 4b to further secure the cover 4a and the traveling arm 4d to the base 4c. Accordingly, the securing structure 4 permits the strap 2 to be fastened more securely to an injured limb than the fit that would be obtained by a procedure in which the user is only permitted to tighten the strap 2 by pulling the free end 2a of the strap 2.

To remove the system 1 from the injured limb L, the user can unlock the lock 4b and can insert his finger into the opening 4j of the cover 4a. The user can then use his finger to lift the cover 4a away from the base 4c, which can cause the projections to disengage the apertures 4h. In another arrangement, a tool can be inserted into the opening 4j, and the user can use the tool to lift the cover away from the base 4c. As the cover 4a is removed from the base 4c, the traveling arm 4d can be forced away from the base 4c, which in turn can direct the supplemental strap 6 and the clamp 3 away from the base 4c as well. As such, the circumference of the loop 2b can be increased slightly.

Finally, the user can disengage the grasping structure 3b to release the strap 2, and the user can then pull the free end 2a of the strap 2, which expands the loop 2b to permit the injured limb L to pass freely through the loop 2b. Thus, the system 1 enables a user with a severely injured and incapacitated limb to stop the severe bleeding associated with such a wound without the assistance of others. It must be noted that the invention is not limited to the above discussion concerning these particular steps and the order in which they are performed. As such, the invention also contemplates a securing structure that can be engaged prior to the engagement of the clamp 3, so long as the securing structure provides supplemental securement to the clamp 3.

Figure 4:
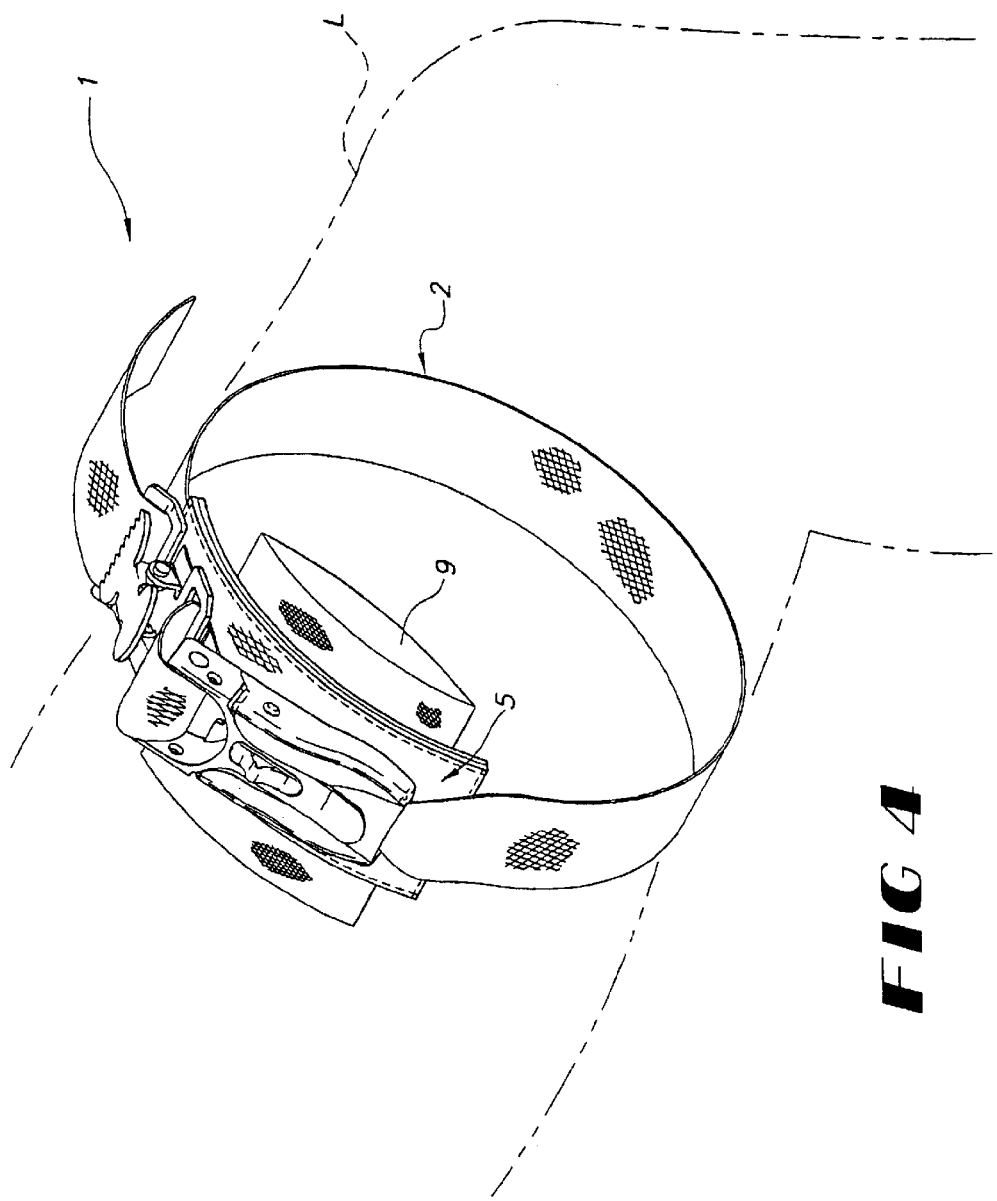
FIG. 4 illustrates the tourniquet system of FIG. 1A positioned around and secured to a person's limb with a bandage positioned between the tourniquet system and the limb.

Referring to FIG. 4, the system 1 can also be used to secure a bandage 9 to a wound. The overall operation is the same as that discussed above; however, the user can place a bandage 9 over a wound and can then place the strap 2 over the bandage 9 before the system 1 is secured to the limb L. Although FIG. 4 shows the bandage 9 as being positioned underneath the elongated base 5, the invention is not so limited, as the bandage 9 can be positioned under any other suitable section of the strap 2. Although not pictured, the system 1, by itself or in combination with one or more other systems 1, could also be used to secure one or more splints to a broken limb such as a broken leg or arm.

Although the present invention has been described in conjunction with the embodiments disclosed herein, it should be understood that the foregoing description is intended to illustrate and not limit the scope of the invention as defined by the claims.

What is claimed is:

1. A tourniquet system capable of being operated by a single user, comprising:

a strap;

a clamp for selectively engaging said strap;

wherein when said clamp engages said strap, said clamp permits said strap to pass substantially freely in a direction away from said clamp and substantially prevents said strap from passing in a direction towards said clamp; and securing structure attached to said strap for securing said strap;

wherein said securing structure further secures said strap when said clamp engages said strap;

wherein said securing structure comprises:

a cover having at least one pin and at least one aperture;

a base having at least one aperture; and a traveling arm having at least one pin;

wherein said cover pin is rotatably coupled to said base apertures;

wherein said traveling arm pin is rotatably coupled to said cover apertures;

wherein said base further comprises a first securing bar and said traveling arm further comprises a second securing bar;

wherein said strap is attached to said first securing bar.

2. The tourniquet system according to claim 1, wherein said securing structure further comprises a lock for securing said cover and said traveling arm to said base.

3. The tourniquet system according to claim 1, wherein said cover further comprises:

a slot for receiving said traveling arm; and an opening for receiving a projection for lifting said cover.

4. The tourniquet system according to claim 1, wherein said tourniquet system further comprises a supplemental strap attached to said clamp and said second securing bar of said traveling arm.

5. The tourniquet system according to claim 1, wherein said strap is constructed of flexible webbing.

6. A tourniquet system capable of being operated by a single user, comprising;

a strap;

a clamp for selectively engaging said strap;

wherein when said clamp engages said strap, said clamp permits said strap to pass substantially freely in a direction away from said clamp and substantially prevents said strap from passing in a direction towards said clamp; and securing structure attached to said strap for securing said strap, wherein said securing structure includes a base and said base further comprises a first securing bar, wherein said strap is attached to said first securing bar;

wherein said base of said securing structure includes at least one aperture, further wherein said securing structure comprises;

a cover having at least one pin and at least one aperture; and a traveling arm having at least one pin;

wherein said cover pin is rotatably coupled to said base apertures;

wherein said traveling arm pin is rotatably coupled to said cover apertures;

wherein said traveling arm further comprises a second securing bar;

wherein said tourniquet system further comprises a supplemental strap attached to said clamp and said second securing bar of said traveling arm.

7. The tourniquet system according to claim 6, wherein said securing structure further secures said strap when said clamp engages said strap.

8. The tourniquet system according to claim 6, wherein said securing structure further comprises a lock for securing said cover and said traveling arm to said base.

9. The tourniquet system according to claim 6, wherein said cover further comprises:

a slot for receiving said traveling arm; and an opening for receiving a projection for lifting said cover.

10. The tourniquet system according to claim 6, wherein said strap is constructed of flexible webbing.

* * * * *